(12) United States Patent
Rezai

(10) Patent No.: US 7,493,168 B2
(45) Date of Patent: Feb. 17, 2009

(54) ELECTRICAL STIMULATION TO TREAT HAIR LOSS

(75) Inventor: Ali R. Rezai, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 409 days.

(21) Appl. No.: 10/503,029

(22) PCT Filed: Feb. 3, 2003

(86) PCT No.: PCT/US03/03210

§ 371 (c)(1),
(2), (4) Date: Jan. 5, 2005

(87) PCT Pub. No.: WO03/063950

PCT Pub. Date: Aug. 7, 2003

(65) Prior Publication Data

US 2005/0107842 A1   May 19, 2005

Related U.S. Application Data

(60) Provisional application No. 60/358,176, filed on Feb. 20, 2002, provisional application No. 60/353,706, filed on Feb. 1, 2002, provisional application No. 60/353,694, filed on Feb. 1, 2002.

(51) Int. Cl.
*A61N 1/00* (2006.01)
(52) U.S. Cl. .......................... 607/50; 607/116; 607/152
(58) Field of Classification Search .................. 604/20, 604/21; 607/50, 139, 152, 116
See application file for complete search history.

(56) References Cited

U.S. PATENT DOCUMENTS

| 4,751,927 | A | * | 6/1988 | Yamada | 606/187 |
|---|---|---|---|---|---|
| 5,336,247 | A | | 8/1994 | Groux et al. | |
| 5,415,629 | A | * | 5/1995 | Henley | 604/20 |
| 5,551,953 | A | * | 9/1996 | Lattin et al. | 604/20 |
| 5,595,564 | A | | 1/1997 | Pinna | |
| 5,782,798 | A | * | 7/1998 | Rise | 604/500 |
| 6,041,262 | A | | 3/2000 | Beder | |
| 6,235,013 | B1 | * | 5/2001 | Tapper | 604/501 |
| 6,332,097 | B1 | | 12/2001 | Beder | |
| 6,520,950 | B1 | * | 2/2003 | Hofmann et al. | 604/503 |
| 6,591,133 | B1 | * | 7/2003 | Joshi | 604/21 |

OTHER PUBLICATIONS http://www.renfrewcenter.com/eating-disorders-anorexia-bulimia/anorexia.asp THe Renfrew Center—Anorexia.*
http://familydoctor.org/online/famdocen/home/common/mentalhealth/eating/063.html Family Doctor.Org—Anorexia Nervosa.*

* cited by examiner

*Primary Examiner*—Mark W Bockelman
(74) *Attorney, Agent, or Firm*—Kenyon & Kenyon, LLP

(57) ABSTRACT

A hair restoration apparatus includes an electrical generator configured to generate an electrical signal meeting defined characteristics. A controller in operative communication with the generator controls operation of the generator and characteristics of the generated electrical signal selected to effect a therapeutically effective application of electrical signals to a hair restoration site. An electrode in electrical communication with the electrical generator is disposed in an area where application of the electrical signal is desired. An electrical connection between the electrical generator and the electrode is provided and sealed for at least partial implantation under the skin of a patient in selected embodiments.

5 Claims, 4 Drawing Sheets

ELECTRICAL STIMULATION TO TREAT HAIR LOSS

CROSS REFERENCE TO RELATED APPLICATIONS

This application claims priority to U.S. Application Ser. No. 60/353,706 filed on Feb. 1, 2002; U.S. Application Ser. No. 60/353,694 filed on Feb. 1, 2002; and U.S. Application Ser. No. 60/358,176 filed on Feb. 20, 2002.

BACKGROUND OF THE INVENTION

The present invention relates generally to the electrical arts. It finds particular application in the medical arts where electrical or chemical stimulation is provided for therapeutic purpose. It will be appreciated however, that the present invention is also amenable to other fields of endeavor where controlled, localized electrical stimulation is desired.

Hair loss is one of the biggest cosmetic concerns facing the society today. It is more common in men but also afflicts the female population. A large number of remedies and preventive measures have been tried for hair loss but still the hope for prevention of hair loss or promotion of hair growth is a difficult and elusive goal. People subject themselves to lengthy, expensive and painful surgeries or expensive use of medications with significant side effects including the growth of hair in unwanted areas.

Androgenetic alopecia, the medical term for male and female pattern baldness was only partially understood until the last few decades. Scientists previously thought it was caused by an overabundance of testosterone. It is now known that dihydrotestosterone (DHT), a derivative of the hormone, is the detrimental agent that causes hair loss. Simply put, under certain conditions DHT "strangles" hair follicles. While this process is the primary cause there are several other factors that contribute to further deterioration of the hair follicle such as: poor-circulation of the scalp, clogged or harshly treated hair follicles, over active sebaceous glands, and nutrient deficient hair follicles.

SUMMARY OF THE INVENTION

In accordance with one aspect of the present invention, an electrical apparatus for treating hair loss includes a power supply capable of selectively generating an electrical signal and a controller in operative connection with the power supply. An electrode mechanism is also provided disposed adjacent to an area of hair loss. The electrode mechanism is in electrical communication with the power supply and is formable by a user to correspond to an area of hair loss.

In accordance with one aspect of the present invention, a hair restoration apparatus includes an electrical generator configured to generate an electrical signal having selected characteristics. A controller in operative connection with the generator controls the operation of the electrical generator and characteristics of the generated electrical signal selected to effect a therapeutically effective application of electrical signal to a hair restoration site. An electrode in electrical communication with the electrical generator is disposed in an area where application of the electrical signal is desired. An electrical connection between the electrical generator and the electrode is sealed for at least partial implantation under the skin of a patient.

DESCRIPTION OF THE DRAWINGS

The invention may take form in various components and arrangements of components and in various steps and arrangements of steps. The drawings are only for purposes of illustrating the preferred embodiments and are not to be construed as limiting the invention. Moreover, the drawings are not to scale and certain elements may be illustrated in exaggerated form for clarity or to illustrate particular features.

DETAILED DESCRIPTION OF THE PREFERRED EMBODIMENTS

Figure 1:
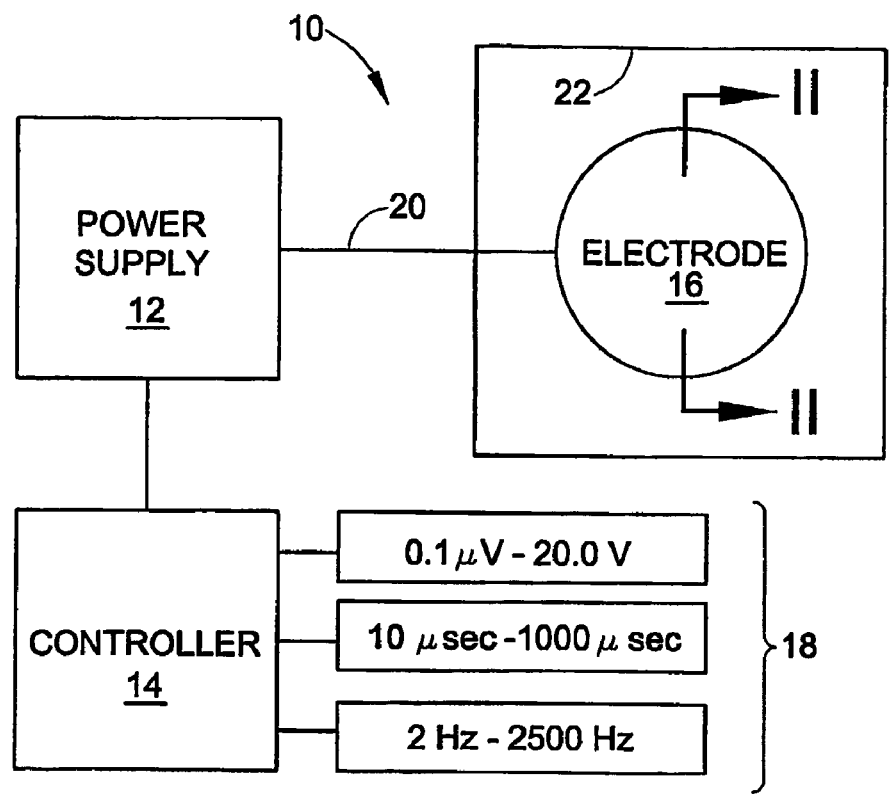
FIG. 1 illustrates a system suitable to practice the present invention.

With reference to FIG. 1, a hair restoration apparatus 10 includes a power supply 12, a controller 14, and an electrode 16. The controller 14 is operatively connected to the power supply and controls the electrical signal output from the power supply 12. Particularly, the electrical signal generated preferably includes a voltage between 0.1 µV and 20 V, a pulse within the range of 10 microseconds to 1000 microseconds, a frequency in the range of 2 Hz to 2500 Hz, and combinations thereof. While the controller 14 is illustrated as a separate component from the power supply 12, those skilled in the art will appreciate that alternate embodiments are possible without departing from the scope of the present invention. These include a controller packaged with a power supply or being an integral part of the power supply and the like. It is further appreciated that when it is desirable to implant the power supply and the controller, a combination of the two components into a single package is often desirable. In the illustrated embodiment of an external controller 14, the electrical signal characteristics are selected via manual switches 18. In alternate embodiments, the electrical signal characteristics are controlled via a microprocessor controlled component of the controller contained, for example, on an application specific integrated circuit (ASIC). In yet further embodiments, an implanted controller is controlled via telemetry, magnetic, radio frequency, and the like control mechanisms. Systems for communicating with implantable medical devices are disclosed for example in U.S. Patent Application No. 20020082665 entitled System And Method Of Communicating Between An Implantable Medical Device And A Remote Computer System Or Health Care Provider and U.S. Patent Application No. 20010012955 entitled Method And Apparatus For Communicating With An Implantable Medical Device, and U.S. Pat. No. 6,201,993 entitled Medical Device Telemetry Receiver Having Improved Noise Discrimination, and are incorporated by reference here for their teachings.

In the illustrated embodiment, power supply 12 is electrically connected with the electrode 16 by an insulated coupling or electrical lead 20. In the case of an externally located power supply and implanted electrode, coupling 20 passes through the skin 22 of a patient to establish electrical conductivity with the implanted electrode 16. In an embodiment, the electrode 16 is formable by cutting, tearing, or separating perforations to substantially conform with the area where treatment is desired. It is to be appreciated that various sizes of electrodes are provided to minimize waste in matching an appropriately sized electrode with the area to be treated such as a hair restoration site.

Figure 2:
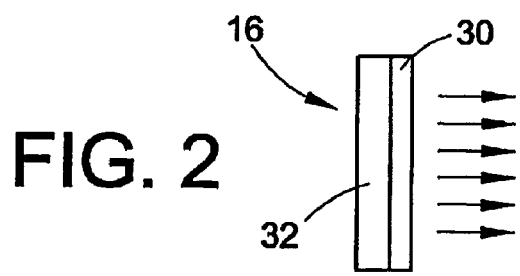
FIG. 2 is a cross sectional view of the electrode taken along lines II-II in FIG. 1.

As best seen by reference to FIG. 2, the electrode is generally flat and includes an identifiable first side 30 placed or implanted such that it lies close or adjacent to the treatment area. In one embodiment, electrode 16 further includes a second side 32 comprising an electrically insulating material to minimize electric field away from the area of interest. In this embodiment, the electric field is substantially directed away from the electrode toward the treatment area (indicated by arrows in FIG. 2) while the electrical field is minimized on the opposite side.

In certain embodiments, particularly non-implanted embodiments, the electrode is externally applied in a pad form, as part of a cap or hair net, or in a grid configuration.

Figure 3:
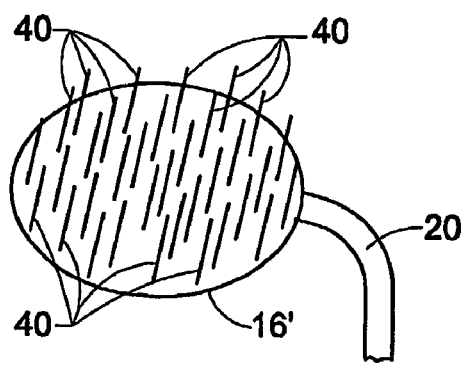
FIG. 3 is a perspective view of an alternative embodiment suitable to practice the present invention.

With reference now to FIG. 3, an electrode 16' is configured with electrically conductive needles or extensions 40 that are gently pressed into the treatment area. In this embodiment, the electrical field generated radiates generally in circular or hemispherical patterns around the needles.

In implantable embodiments, the electrode inserted beneath the treatment area as further explained below. In still other embodiments, the electrode is surgically placed in an area of the hypothalamus using, for example, deep brain surgical techniques as know by neuro surgeons and skilled artisans. Preferably such an implant is programmed to disrupt the production of testosterone or derivatives thereof.

Figure 4:
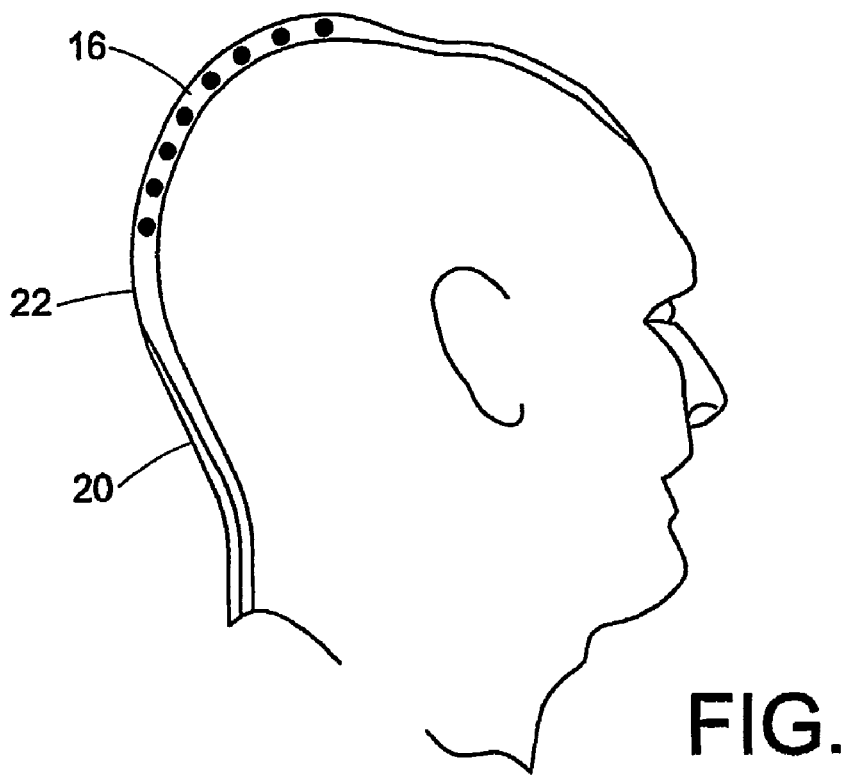
FIG. 4 is a side view of a subcutaneous implant.

With reference now to FIG. 4, the electrode 16 is placed subcutaneously. It is now apparent that such a placement can be achieved through a small incision and subsequent insertion of a folded electrode. The procedure is completed by unfolding or forming the electrode beneath the skin with only the electrical lead 20 protruding. As discussed above, alternate embodiments include an entirely implanted system where the insulated coupling extends from the electrode subcutaneously to an implanted power supply.

Figure 5:
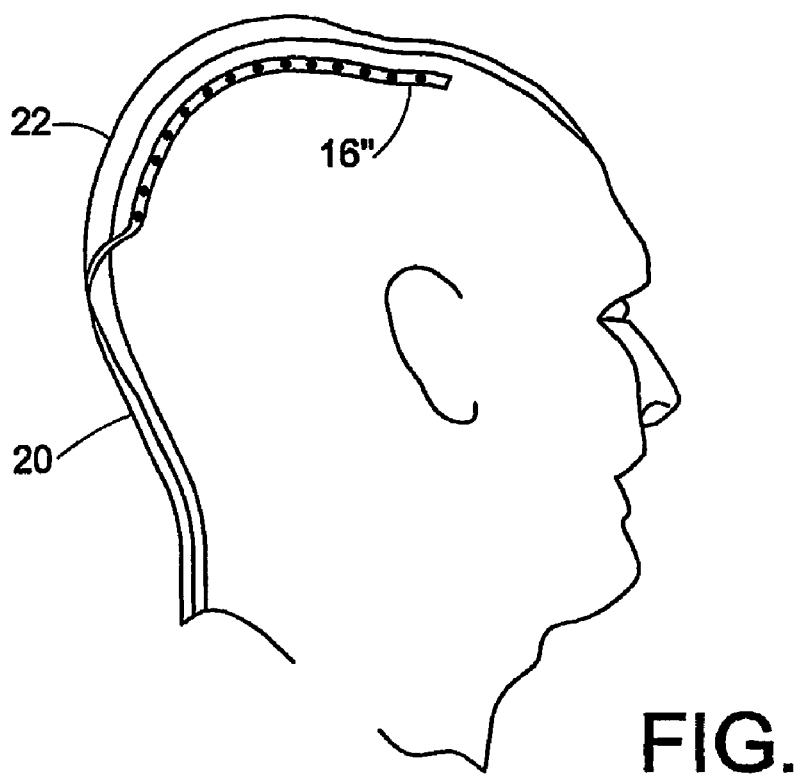
FIG. 5 is a side view of a subgaleal implant.

With reference now to FIG. 5, an electrode array 16" is effective as a subgaleal implant. Such an implant is most preferably achieved by inserting a folded electrode array and subsequently forming or spreading the array in place.

Figure 6:
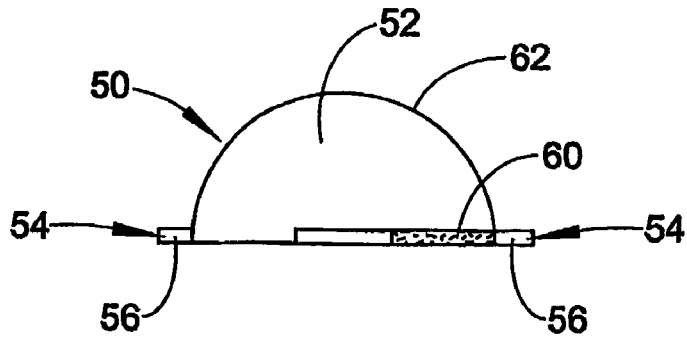
FIG. 6 illustrates a dome infusion reservoir.

With reference now to FIG. 6, another embodiment of the present invention provides a microinfusion system 50 including a domed-type chamber or reservoir 52 which in the illustrated embodiment can contain a single medication. Multiple dose chambers are also within the skill of an artisan. The system further includes a base 54 having a radius larger than the base of the reservoir 52. Incorporated into the base 54 are outlets 56 at opposing sides of the reservoir 52. Those skilled in the art can appreciate that in alternative embodiment, many outlets may be spaced about the periphery of the base 54. The system also includes a dose control 60 which regulates the rate of medication to outlets 56.

In one embodiment of the invention illustrated in FIG. 6, the exterior shell 62 of the reservoir 56 includes a penitratable surface such that a hypodermic needle, for example, may be used to replenish a medication supply without removing the entire system.

In an alternate embodiment, the system illustrated in FIG. 6 is a single use, preloaded system which remains in place until the supply of medication is exhausted. Those of ordinary skill in the art can recognize that the size of such a system permits subcutaneous implantation, both for cosmetic reasons and to place the medication closer to the area where needed.

Figure 7:
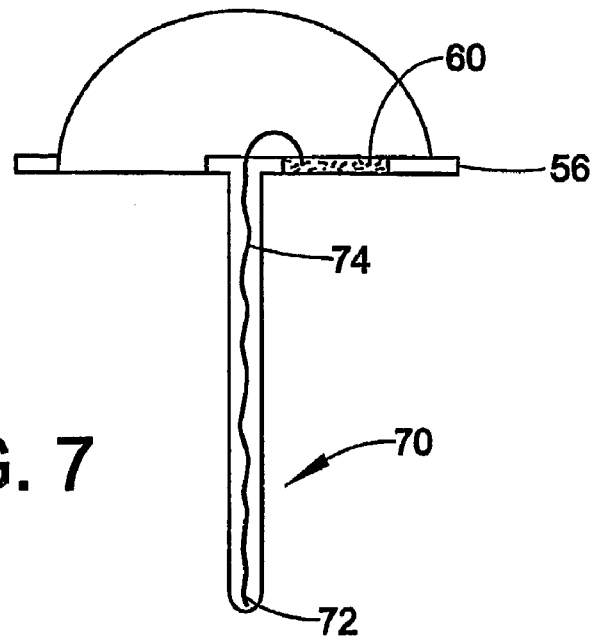
FIG. 7 illustrates an alternate dome infusion reservoir.

With reference now to FIG. 7, an alternate embodiment of the system includes an extended catheter tip 70 for depositing medication to a deep or remote location such as in deep brain infusion. Also illustrated is a sensing embodiment. A fiber optic or other sensor 72 is included for sensing the medication at the point of interest. A feedback loop 74 permits the dose controller 60 to adjust the rate of medication delivery depending on the sensed data. As is now evident from continued reference to FIG. 2, medication can alternately flow from both the extended catheter 70 as well as outlets 56.

Figure 8:
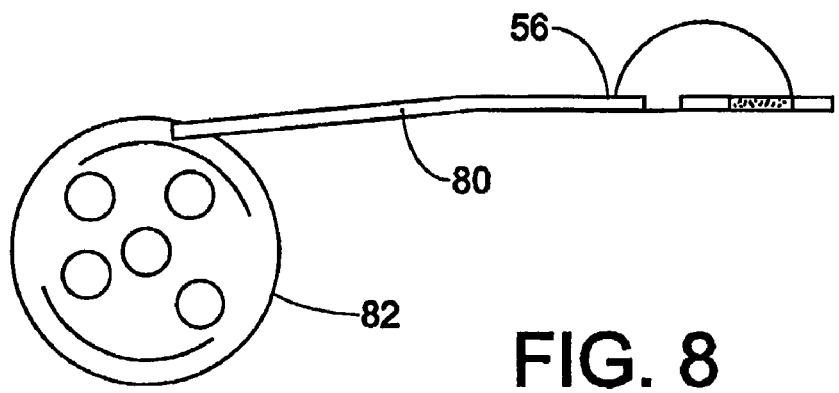
FIG. 8 illustrates a catheter tip with capability for perineural insertion.

Referring now to FIG. 8, the system is shown with a catheter 80 connected to outlets 56. As is apparent from FIG. 8, the catheter may be inserted into an area of interest, such as a peripheral nerve 82 as illustrated.

In one embodiment, the device consists of a domed type chamber which may have septations to allow the introduction of one, two, or multiple drugs into an area of interest including the central or peripheral nervous system with a microcatheter, or an area directly on the scalp. The device in one embodiment can also have a fixed or electronically adjustable valve system to allow a particular dosing of the drug. In another embodiment, there are sensors at the output end of the chamber providing feedback to automatically adjust the dosing. Additionally, this system can be attached to currently existing deep brain stimulation burr hole devices.

In an alternate embodiment, the device comprises the actual burr hole ring. For example, the circle of the ring will include a chamber or reservoir with a port for injection and a tab or notch for insertion of a cannula and a notch for insertion of an electrode.

The system in its one form would be a disposable system for fixed dosing a single medication which could be implanted in a patient as a tool for trial chemical modulation. Prior to the present invention, this was accomplished through the implantation of a large and bulky drug delivery system having a diameter of about 7.5 cm.

In other forms the system is semi-permanent and reusable but still more compact than present drug delivery systems.

The system is smaller than that which is presently available which is advantageous when delivering drug/chemical within the substrate of the entral or peripheral nervous system. Also, dosing concentrations for direct nervous system injection are in order of magnitude smaller than either oral, intravenous, or intrathecal dosages.

In yet other forms, the system allows the delivery of multiple types of drugs, chemicals, medication and the like. The system allows controlled medication delivery such that a microinfusion device adds drugs, neurotransmitters, Rogaine, or other such material to the local environment at a determined rate. Moreover, other embodiments include combinations of electrical and chemical neuromodulation. The chemical agent may be a neurotransmitter mimic; neuropeptide; hormone; pro-hormone; antagonist, agonist, reuptake inhibitor, or degrading enzyme thereof; peptide; protein; therapeutic agent; nucleic acid; or stem cell and may be delivered by a slow release matrix or drug pump. Although such chemical agents are generally administered orally in traditional pharmacotherapies, by directly stimulating the target sites that synthesize or release such products, low and precise doses of the chemical agents can be administered so as to minimize or avoid the side effects and delayed onset of relief common to traditional pharmacotherapy.

The system is subcutaneously implantable.

The system can be utilized for delivery of drugs/chemicals/gene therapy vectors/viral vectors into the central or peripheral nervous system.

Dosed delivery of chemotherapy or antibiotic over the course of many days to weeks.

The applications of the invention includes drug delivery for Parkinson's-Disease Essential tremor, MS, Dystonia, cerebral palsy, psychiatric disorders, obsessive compulsive disorder, depression, Mucimol, Dystonia, ALS, Gene therapy vectors to allow delivery of substance retrograde through the peripheral nerves. Controlled antibiotic therapy for meningitis bacterial or chemical. Chemotherapy for carcinomatous meningitis, or central nervous system lymphoma or other metastatic disease.

Another embodiment of the present invention includes set of compact RF compatible receiving coils or a smaller temporary impulse generator which is coupled to an already implanted deep brain stimulator electrodes, other neurostimulation electrodes such as those used for motor cortex or spinal cord stimulation, or generally to implanted electrodes anywhere. This compact receiving RF coil or smaller temporary impulse generator can be implanted in the subgaleal space and can be externally stimulated with an accessory external antenna (outside of the skin) connected to a battery powered transmitter (in the case of an RF system). Such coil systems permit externally applied signals to be communicated to electrodes without dedicated pulse generators in each instance or otherwise when dedicated generators are undesirable.

Figure 9:
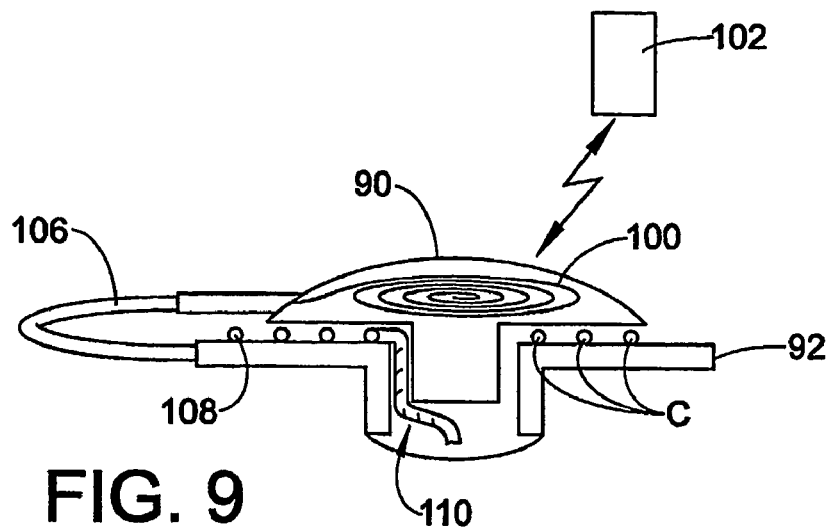
FIG. 9 is a cross-sectional view of a stimulator device suitable to practice an aspect of the present invention.

With reference now to FIG. 9, a neurostimulator according to one embodiment of the present invention includes a cap 90 which rests snugly in a burr hole ring 92 overlaying a region of interest. Disposed within cap 90 are antenna windings 100 which are suitable for receiving RF radiation from a transmitter 102. A lead 106 from winding 100 connects with windings 108 associated with burr ring 92. In the illustrated embodiment, burr ring 92 includes a plurality of channels C in which the windings reside. At an end of channel C towards central opening 110 the implanted electrode is electrically connected to the winding 108. As those skilled in the art can appreciate, this completes the electrical connection between the coil or winding 100 and the electrode tip disposed in the treatment site (not shown). It can now be appreciated that other electrode locations are possible without departing from the scope of the invention.

Figure 10:
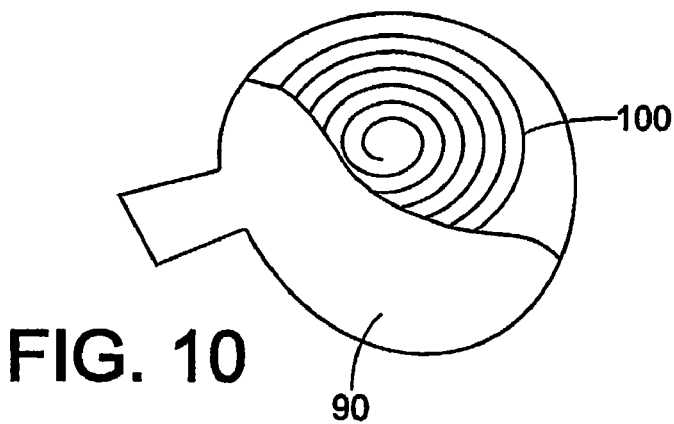
FIG. 10 is a view of a stimulator device.

With reference now to FIG. 10, a plan view of the cap 90 is illustrated partially cut away to reveal windings 100 disposed therein. As those skilled in the art can appreciate, the cap is preferably made from a material which will readily pass the received RF energy to the coil or windings 100 disposed within.

Figure 11:
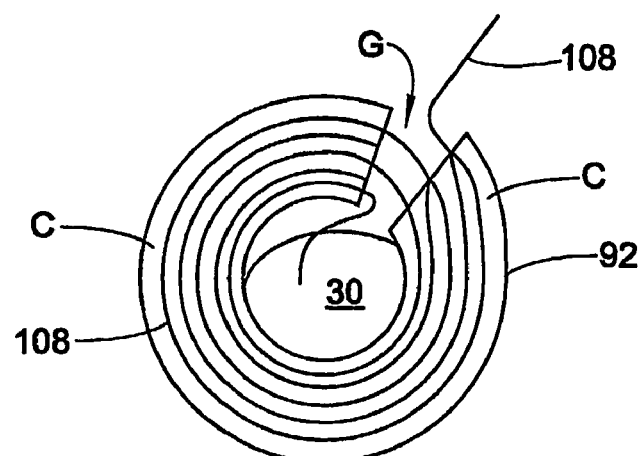
FIG. 11 is a view of a burr hole ring with three groves.

With reference now to FIG. 11, a plan view of the burr ring 92 reveals a channel C through which the winding 108 is wrapped. The ring has a gap G permitting, among others, custom and secure fit within the burr hole.

Desirably, its smaller size would allow for its implantation into the head or via a small incision after the insertion of a percutaneous spinal cord stimulator system. Additionally, It would be cheaper and smaller than the currently available totally implantable pulse generators.

With respect to particular details of electrical stimulation according to aspects of the present invention, once the electrode is secured at the target site, the stimulation controller is activated thereby applying to the target site an oscillating electrical signal having specified pulsing parameters. The oscillating electrical signal may be applied continuously or intermittently and the pulsing parameters, such as the pulse width, amplitude, frequency, voltage, current, intensity, and/or waveform may be adjusted to affect a desired result. Preferably, the oscillating electrical signal is operated at a voltage between about 0.1 µV to about 20 V. More preferably, the oscillating electrical signal is operated at a voltage between about 1 V to about 15 V. Preferably, the electric signal is operated at a frequency range between about 2 Hz to about 2500 Hz. More preferably, the electric signal is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar, bipolar when the electrode is bipolar, and multipolar when the electrode is multipolar. In addition, we can generate various waveforms such as sine wave and others in addition to the square wave forms of stimulation.

Notwithstanding whether chemical and/or electrical stimulation is employed in embodiments of the present invention, also contemplated are use of a closed-loop feedback mechanism in conjunction with chemical stimulation, electrical stimulation, or both. Such physiological activity to be detected is a physiological characteristic or function of the body, and includes, for example, testosterone, estrogen or one of their metabolites level being detected in the body, blood, subcutaneous tissue, and the like.

The description above is intended to provide illustrations of some of the presently preferred embodiments of the invention. In light of the above description and examples, various other modifications and variations will now become apparent to those skilled in the art without departing from the spirit and scope of the present invention as defined by the appended claims. For example, disorders treatable by the present invention include hyperandrogenic Alopecia—occuring for example in premenopausal females, Alopecia Aerata, Androgenetic Alopecia, Drug indued Alopecia, Alopecial Aerata, and the like. Accordingly, the scope of the invention should be determined solely by the appended claims and the equivalents thereof.

Having thus set forth the preferred embodiments, I claim:

1. A method of treating hair loss in a patient suffering from hair loss, comprising:
   providing an electrode having a conductive side and an insulated side;
   surgically implanting the electrode under the skin of the patient adjacent the hair loss are such that the implanted conductive side faces the hair loss area and the implanted insulated side faces away from the hair loss area, wherein an electric field generated by the electrode is directed substantially towards the hair loss area;
   generating an electrical signal;
   adapting the electrical signal to comprise a voltage in the range of 0.1 microvolts to 20 volts;
   coupling the adapted electrical signal to the electrode; and
   applying the adapted electrical signal through the electrode to the hair loss area and treating said hair loss.

2. The method as set forth in claim 1, further comprising:
   adapting the electrical signal to comprise a frequency in the range of 2 hertz to 2500 hertz.

3. The method as set forth in claim 1, further comprising:
   adapting the electrical signal to comprise a pulse width in the range of 10 microseconds and 1000 microseconds.

4. The method as set forth in claim 1, further comprising extending a lead from the electrode for connection to an electrical signal generator.

5. The method of claim 1, further comprising;
   conforming the shape of the electrode to the hair loss area.

* * * * *